United States Patent [19]
Rüschoff et al.

[11] Patent Number: 6,150,100
[45] Date of Patent: Nov. 21, 2000

[54] METHOD FOR THE DETECTION OF MICROSATELLITE INSTABILITY FOR TUMOR DIAGNOSTICS

[75] Inventors: Josef Rüschoff, Bad Abbach; Wolfgang Dietmaier, Regensburg, both of Germany; Richard Fishel, Penn Valley, Pa.

[73] Assignee: Roche Diagnostics GmbH, Mannheim, Germany

[21] Appl. No.: 09/047,347

[22] Filed: Mar. 25, 1998

[30]       Foreign Application Priority Data

Mar. 25, 1997 [DE] Germany ................ 197 12 332

[51] Int. Cl.[7] .............. C12Q 1/68; C12P 19/34; C07H 21/04
[52] U.S. Cl. ............ 435/6; 435/91.2; 536/24.33
[58] Field of Search ............ 435/6, 91.2; 536/24.33

[56]                References Cited

U.S. PATENT DOCUMENTS

| | | | |
|---|---|---|---|
| 5,582,979 | 12/1996 | Weber | 435/6 |
| 5,702,886 | 12/1997 | Vogelstein | 435/6 |

FOREIGN PATENT DOCUMENTS

WO 94/19492 9/1994 WIPO.

OTHER PUBLICATIONS

Luceri et al. Proc. Ann. Meet. Am. Assoc. Cancer Res. 38:A3061, Mar. 21, 1997.
Liu et al. Nature Med. 2(2):169–174, Feb. 1996.
Hoang et al. Cancer Res. 57:300–303, Jan. 1997.
Liu et al. Nature Med. 1(4):348–352, Apr. 1995.
Papadopoulos et al. Science 268:1915–1917, Jun. 1995.
Grogan et al. Hist. Histopathol. 11:807–820, 1996.
Futreal et al. Nucleic Acids Res. 19(24):6977, 1991.
Gyapay et al. Nature Genetics 7:246–339, Jun. 1994.

Primary Examiner—Carla J. Myers
Assistant Examiner—Diana Johannsen
Attorney, Agent, or Firm—Arent Fox Kintner Plotkin & Kahn PLLC

[57]                ABSTRACT

The invention concerns a method for the determination of the genomic instability at 5 selected microsatellite loci. The analysis of these selected loci is suitable for making prognostic tumour diagnoses, for analysing hereditary tumor predisposition as well as for early tumor detection. This method is of particular importance for the diagnosis of tumors of the gastrointestinal tract such as colorectal tumors.

73 Claims, 6 Drawing Sheets

Fig.1

| Fig.1a |
|---|
| Fig.1b |

Fig.1a

| LOCUS SYMBOL | PCR-Tm | SEQ. ID NO. | MARKER NAME | CHROM. LOC. | PRIMER SEQUENCE | MOTIF | FRAGMENT LENGTH (bp) | REFERENCE |
|---|---|---|---|---|---|---|---|---|
| D2S123 | 60 | 1 | AFMO93xh3 | 2p16 | AAA CAG GAT GCC TGC CTT TA | CA | 197-227 | WEISSENBACH, J NATURE 359:794-801 1992 |
| D2S123 | | 2 | | | GGA CCT TCC ACC TAT GGG AC | | | |
| D3S1283 | 60 | 3 | AFM163yc3 | 3p24.2/22 | GGC AGT ACC ACC TGT AGA AAT G | CA | 150-160 | WEISSENBACH, J NATURE 359:794-801 1992 |
| D3S1283 | | 4 | | | GAG TAA CAG AGG CAT CGT GTA TTC | | | |
| D5S346 | 55 | 5 | LNS-CA 1 (APC) | 5q21/22 | ACT CAC TCT AGT GAT AAA TCG | CA | 96-122 | SPIRIO,L NUCL. ACIDS RES. 1:6348 1991 |
| D5S346 | | 6 | | | AGC AGA TAA GAC AGT ATT ACT AGT T | | | |
| D9S171 CA | 60 | 7 | AFM-186xc3a | 9p21 | AGC TAA GTG AAC CTC ATC TCT GTC T | CA | 159-177 | WEISSENBACH, J NATURE 359:794-801 1992 |
| D9S171 GT | | 8 | | | ACC CTA GCA CGT ATG GTA TAG TCT | | | |
| D1DS89 | 55 | 9 | Mfd28CA | 10pler | AAC ACT AGT GAC ATT ATT TTC | CA | 142-156 | WEBER, J.L. NUCL.ACIDS RES. 1:4637 1990 |
| D1DS89 | | 10 | | | AGC TAG GCC TGA AGG CTT CT | | | |
| D1DS197 CA | 65 | 11 | AFM118xh12a | 10qler | ACC ACT GCA CTT CAG GTG AC | CA | 161-173 | WEISSENBACH, J NATURE 359:794-801 1992 |
| D1DS197 GT | | 12 | | | GTG ATA CTG TCC TCA GGT CTC C | | | |
| D11S904 CA | 58 | 13 | AFM081za5 | 11p14/13 | ATG ACA AGC AAT CCT TGA GC | CA | 185-201 | WEISSENBACH, J NATURE 359:794-801 1992 |
| D11S904 GT | | 14 | | | CTG TGT TAT ATC CCT AAA GTG GTG A | | | |
| D11S1316 | 52 | 15 | AFM218xela | 11p155 | CCC GTA TGG CAA CAG G | CA | ca 130 | GYAPAY, G NATURE GENET. 7:246-339 1994 |
| D11S1316 | | 16 | | | TGT GCA TGT NCA TGA GTG | | | |
| D13S175 CA | 60 | 17 | AFM249xbla | 13q11 | TAT TGG ATA CTT GAA TCT GCT G | CA | 101-113 | WEISSENBACH, J NATURE 359:794-801 1992 |
| D13S175 GT | | 18 | | | TGC ATC ACC TCA CAT AGG TTA | | | |
| D17S250 | 52 | 19 | Mfd15CA | 17q11.2-q12 | GGA AGA ATC AAA TAG ACA AT | CA | ca 150 | WEBER, J.L. el al, NUCL. ACIDS RES. 18:4640 1990 |
| D17S250 | | 20 | | | GCT GGC CAT ATA TAT ATT TAA ACC | | | |
| D17S26 | 58 | 21 | Mfd41 | 17p12-11.1 | CAG GTT CTG TCA TAG GAC TA | CA | 157-171 | WEBER, J.L. el al, NUCL. ACIDS RES. 18:4640 1990 |
| D17S26 | | 22 | | | TTC TGG AAA CCT CTT ACT CCT GA | | | |
| D18S69 | neg. | 23 | Mfd26CA | 16q12 | CAG AAA ATT CTC TCT GGC TA | CA | 103-119 | STRAUB, R.E. GENOMICS 15:48-56 1993 |
| D18S69 | | 24 | | | CTC ATG TTC CTG GCA AGA AT | | | |

Fig.1b

| Marker | | SEQ ID | Name | Locus | Sequence | Repeat | Size | Reference |
|---|---|---|---|---|---|---|---|---|
| D18S58 | 53 | 25 | AFM164xe31a | 18q22.3 | GCTCCCGGCTGGTTT T | CA | 144-160 | Dib, C. NATURE 380:152-154, 1996 |
| D18S58 | | 26 | | | GCAGGAAATCGCAGGAACTT | | | |
| D18S69 | 60 | 27 | AFM248yl1 | 18q21 | CTC TTT CTC TGA CC | CA | ca. 110 | WEISSENBACH, J NATURE 359:794-801 1992 |
| D18S69 | | 28 | | | GAC TTT CTA AGT TCT TGC CAG | | | |
| | 72 | 29 | AR"234" | Xcen-q13 | AGC GCA GCA CCT CCC GGC GCC AGT T T | CAG | ca. 125 | |
| | | 30 | AR"235" | | GCT GCT GCT GCC TGG GGC TAG TCT CTT | | | |
| | 58 | 31 | BAT-25 | 4q12 | TCG CCT CCA AGA ATG TAA GT | A25 | ca. 90 | PAPADOPOULOS, N. et al SCIENCE 268:1915-1917 |
| | | 32 | BAT-25 | | TCT GCA TTT TAA CTA TGG CTC | | | |
| | 56 | 33 | BAT-26 | 2p | TGA CTA CTT TTG ACT TCA GCC | A26 | ca. 80-100 | PAPADOPOULOS, N. et al SCIENCE 268:1915-1917 |
| | | 34 | BAT-26 | | AAC CAT TCA ACA TTT TTA ACC C | | | |
| | 58 | 35 | BAT-40 | 1p13.1 | ATT AAC TTC CTA CAC CAC AAC | A40 | ca. 80-100 | PALSONLICHE MITTERLUENG VON DR. RICHARD FISHEL |
| | | 36 | BAT-40 | | GTA GAG CAA GAC CAC CTT G | | | |
| | 72 | 37 | FMR2 | X | CGG TTA TCC CAG TTC GGC CTC TCT GGG AT | CAAAC | 172 | |
| | | 38 | FMR2 | | TCC ACC TCC CGC TCA GTC AGA CTG CGC T | | | |
| | 60 | 39 | HPRT1 | Xq26 | GCA GCT ATA ATG ACT AGA ATG AAG TCC TAC TG | GATT | 151-163 | RESEARCH GENOLICS (HUNTSVILLE, AL) |
| | | 40 | HPRT1 | | TTG AAT TAA AGA CTT GTT TAA ACA CAA AAT TTA GAC | | | |
| | 53 | 41 | MYCL1- | 1p32 | TGG CGA GAC TCC ATC AAA G | AAAG | 140-209 | MAKETA, T.P. et al HOM MOL GENET. 1.217 1992 |
| | | 42 | MYCL1- | | CTT TTT AAG CTG CAA CAA TTT C | | | |
| | 58 | 43 | RB- | 13q14 | CTC CTC CCT ACT TAC TTG T | CTTTTT | 260-300 | HUANG, CANCER RES. 52:6525, 1992 |
| | | 44 | RB- | | AAT TAA CAA GGT GTG GTG G | | | |
| | 58 | 45 | lp53Alu | 17p13.1 | GCA CTT TCC TCA ACT CTA CA | AAAAT | ca. 400 | FUTREAL, NUCL ACIDS RES. 19:6977 1991 |
| | | 46 | lp53Alu | | AAC AGC TCC TTT AAT GGC AG | | | |
| | 65 | 47 | TP53.PCR | 17p13.1 | AGG GAT ACT ATT CAG CCC GAG GTG | CA | 103-135 | JENES,M.H. GENES CHROM. CANCER 5:89-90 1992 |
| | | 48 | | | ACT GCC ACT CCT TGC CCC ATT C | | | |
| | 63 | 49 | TBP- | 6q27 | CCC ACA GCC TAT TCA GAA CAC | CAG | 185-206 | POLYMEROPOULOS et al. NUCL. ACIDS RES. 19:4307 1991 |
| | | 50 | TBP- | | GTT GAC GTC TGA ACG GCT GC | | | |

Fig.5

| PATIENT | DATE OF BIRTH | AGE | ALIVE | T | N | M | G | LOC | CLASS EX. 1 |
|---|---|---|---|---|---|---|---|---|---|
| 1 | 22.02.12 | 80 | NO | 4 | 3 | X | 3 | ri | RER+ |
| 2 | 23.01.49 | 44 | YES | 3 | 0 | 0 | 2 | ri | RER+ |
| 3 | 10.09.28 | 64 | YES | 2 | 0 | 0 | 2 | R | RER- |
| 4 | 09.02.19 | 74 | YES | 2 | 0 | 0 | 2 | ri | RER- |
| 5 | 20.08.28 | 64 | YES | 3 | 1 | X | 3 | R | RER+ |
| 6 | 04.06.29 | 64 | NO | 4 | 0 | 0 | 3 | R | RER- |
| 7 | 15.06.37 | 56 | YES | 3 | 0 | 1 | 2 | R | lowMin+ |
| 8 | 25.11.24 | 70 | YES | 2 | 1 | 0 | 3 | ri | RER+ |
| 9 | 31.07.19 | 74 | NO | 4 | 0 | 0 | 3 | R | RER- |
| 10 | 22.06.29 | 64 | NO | 3 | 2 | 0 | 2 | le | RER- |
| 11 | 31.03.41 | 52 | YES | 0 | 0 | 0 | 2 | R | RER- |
| 12 | 30.04.46 | 47 | YES | 3 | 1 | 0 | 2 | R | RER- |
| 13 | 13.08.36 | 57 | YES | 3 | 1 | 0 | 3 | ri | RER+ |
| 14 | 03.09.28 | 65 | YES | 3 | 0 | 0 | 2 | R | RER- |
| 15 | 14.07.34 | 59 | YES | 1 | 0 | 0 | 2 | R | RER- |
| 16 | 22.07.09 | 84 | NO | 3 | 0 | 0 | 2 | ri | RER+ |
| 17 | 19.11.16 | 78 | NO | 3 | 2 | X | 2 | R | RER- |
| 18 | 13.03.50 | 44 | YES | is | 0 | 0 | 2 | le | RER- |
| 19 | 08.06.23 | 70 | YES | 2 | 0 | 0 | 2 | R | RER- |
| 20 | 01.07.37 | 57 | NO | 2 | 0 | X | 2 | ri | lowMin+ |
| 21 | 01.07.37 | 57 | NO | 3 | 2 | 0 | 3 |  | RER- |
| 22 | 03.06.33 | 60 | NO | 4 | 2 | 1 | 3 | ri | RER- |
| 23 | 06.02.22 | 72 | YES | is | 0 | 0 | 2 | ri | RER- |
| 24 | 30.10.35 | 59 | NO | 4 | 3 | 1 | 3 | le | RER- |
| 25 | 29.04.12 | 82 | NO | 3 | 3 | 1 | 2 | R | RER- |
| 26 | 17.07.21 | 73 | YES | 3 | 1 | 0 | 3 | ri | RER- |
| 27 | 21.12.55 | 39 | NO | 3 | 2 | 1 | 3 | R | RER- |

METHOD FOR THE DETECTION OF MICROSATELLITE INSTABILITY FOR TUMOR DIAGNOSTICS

The invention concerns a method and a kit for the prognostic diagnosis, predisposition diagnosis and early recognition of tumours of the gastrointestinal tract preferably colorectal tumours. The basis for this is the detection of the genomic instability of so-called microsatellites with the aid of PCR.

Microsatellites (MIS) are short tandem repeats which are distributed over the entire human genome. Microsatellites occur statistically about once every 100,000 base pairs. Up to now 5 classes of MIS have been described which differ from one another in the length of their smallest repetitive unit as a mono-, di-, tri-, tetra- or pentanucleotide repeat. As a rule these repetitive units occur repeatedly 10 to 40 times in a tandem arrangement. Microsatellite instability (MIN) in the form of small deletions or insertions can be detected in many tumour patients if one compares DNA from tumour material with normal DNA of the same individual (Thibodeau et al., (1993), Science, 260, 816–819) (WO 94/19492). This is achieved by amplifying the DNA with the aid of PCR and subsequently separating the amplification products by gel electrophoresis. A permanent replication defect of the tumour cells is regarded to be the cause of MIN (Parsons et al., (1993), Cell, 75, 1227–1236; Shibata et al., (1994) Nat. Genet. 6, 273–281). Such tumours are classified as "replication error-positive" (RER+). An RER+ phenotype is characteristic for colorectal tumours in families with HNPCC (hereditary non-polyposis colon cancer) (Aaltonen et al., (1993), Science, 260, 812–816).

The analysis of microsatellites is an extremely attractive method for diagnostic applications as well as for the examination of the tumourigenesis of RER+ tumours. Because it is simple to carry out the determination of MIN before sequencing the mismatch repair gene of HNPCC families is a suitable aid in identifying potential RER+ patients. MIN analysis is also of major importance for the prognostic diagnosis of sporadic colorectal carcinoma because the occurrence of MIN correlates with a better prognosis (Lothe et al. (1993) Cancer Res., 53, 5849–5852; Thibodeau et al. (1993), Science, 260, 816–819; Bubb et al. (1996) Oncogene, 12, 2641—2649).

MIN can be detected in more than 90% of all HNPCC tumours (Liu et al., (1996) Nature Med., 2, 169–174) whereas MIN only occurs with a frequency of 10–20% in sporadic colorectal tumours (Thibodeau et al. (1993) Science, 260, 816–819; Ionov et al. (1993), Nature, 363, 558–561; Aaltonen et al. (1993) Science, 260, 812–816; Lothe et al. (1993) Cancer Res., 53, 5849–5852). However, MIN is not restricted to colorectal tumours but has also been detected in other tumours. These include among others pancreatic carcinomas (Han et al. (1993) Cancer Res., 53, 5087–5089), gastric carcinomas (Han et al. (1993) Cancer Res., 53, 5087–5089; Peltomaki et al. (1993) Cancer Res., 53, 5853–5855; Mironov et al. (1994) Cancer Res., 54, 41–44; Rhyu et al. (1994) Oncogene, 9, 29–32; Chong et al. (1994) Cancer Res., 54, 4595–4597), prostate carcinomas (Gao et al. (1994) Oncogene, 9, 2999–3003), carcinomas of the endometrium (Risinger et al. (1993) Cancer Res., 53, 5100–5103; Peltomaki et al. (1993) Cancer Res., 53, 5853–5855) and mammacarcinomas (Patel et al. (1994) Oncogene, 9, 3695–3700).

The mechanism of the tumourigenesis of RER+ tumours is not known in detail. Up to now five genes have been identified whose defect can lead to an occurrence of the RER+ phenotype. Since genetic variabilities for hMLH1 (Bronner et al. (1994) Nature, 368, 258–261) and also for hMSH2 (Fishel et al. (1993) Cell, 75, 1027–1038; Leach et al. (1993) Cell, 75, 1215–1225) have been detected in HNPCC families with a frequency of over 30%, these two genes apparently play an important role in the expression of MIN. Two other mismatch repair genes, hPMS1 and hPMS2 are mutated in less than 5% of all HNPCC patients so that these genes have a relatively secondary role in RER+ tumours. However, it may be assumed that further previously unknown genes are involved in an effective mismatch repair.

There is reason to assume that MIN plays a direct role in tumourigenesis because defects in the mismatch repair system result in mutations in microsatellites in the coding region of genes that are important for the regulation of cell proliferation. For example a repeat of 10 deoxyadenosines in the coding region of the TGFbeta 1 receptor gene has been identified as a MIN target (Markowitz et al., (1995) Science, 268, 1336–1338). A further MIN target, the IGF(II)R gene, is mutated at a $(G)_8$ repeat within its coding region in gastrointestinal tumours (Souza et al. (1996) Nat. Genet., 14, 255–257). Interestingly only 10% of all examined tumours with MIN were mutated in both genes. Another $(G)_8$ MIS within a histone gene was not mutated in any of the examined tumours (Souza et al. (1996) Nat. Genet. 14, 255–257). Moreover up to now it was possible to detect MIN only at some of the examined loci. Whether and to what extent microsatellites which have already been shown to be unstable differ with respect to the frequency of the occurrence of MIN was not known at the time of the invention.

On the contrary there is no further basis for the selection of suitable loci to analyse MIN. Hence it is not known whether and if so which loci are most suitable for an unequivocal determination of RER+ phenotypes. In contrast the state of the art is to analyse 4 to 7 arbitrarily selected loci to classify the MIN status for example in colorectal carcinomas (e.g. Aaltonen et al. (1993) Science, 260, 812–816; Thibodeau et al. (1993) Science, 260, 816–819; Lothe et al. (1993) Cancer Res., 53, 5849–5852; Kim et al. (1994) Am. J. Path., 145, 148–156; Bubb et al. (1996) Oncogene, 12, 2641–2649; Plummer and Casey, (1996) Nat. Med., 2, 156–158).

In these methods mononucleotide and dinucleotide loci are analysed most frequently. In this connection dinucleotide repeat loci can be divided into 2 different, classes:

Non-complex loci which do not have any further repetitive elements apart from the dinucleotide repeat within the region to be amplified (class 2a). These loci include APC, D13S175; D3S1283, Mfd26, Mfd28 and Mfd41.

Complex loci in which further repetitive sequences occur in addition to the dinucleotide repeat (class 2b). These loci include Mfd15, D10S197, D11S1318, D11S904, D18S69, D2S123, D9S171 and TP53PCR.

In addition mononucleotide repeat loci have also been examined several times since they are easy to amplify and yield unequivocal gel electrophoretic signals (Liu et al. (1996) Nature Med., 2, 169–174; Augenlicht et al. (1996) Oncogene, 12, 1767–1772; Plummer and Casey, (1996) Nat. Med., 2, 156–158).

Hence the basis for the invention was the search for polymorphic loci whose analysis enables reliable information to be obtained on the general tendency for genomic instability. In this connection it has been possible to detect different frequencies of polymorphic changes at different microsatellites on which MIN have already been found by the state of the art. Moreover, it was also determined that in different patients different classes of microsatellites are affected with different frequencies of genomic instability. Consequently an analysis of different classes of MIS is essential for a reliable determination of the RER phenotype with a limited number of PCR reactions.

The invention therefore concerns a method for the diagnosis of tumours for the analysis of microsatellite loci comprising the following steps:

a) Isolation of genomic DNA from human biological material b) DNA amplification of 5 different microsatellite loci with the aid of 5 different primer pairs in each case characterized in that the loci to be amplified are two mononucleotide repeat loci, one or two dinucleotide repeat loci of class 2a, one or two dinucleotide repeat loci of class 2b and zero to one pentanucleotide repeat locus.

c) Size determination of the amplification products

An embodiment has proven to be particularly advantageous in which the 5 microsatellite loci to be analysed are selected from a group of loci comprising: BAT25, BAT26, BAT40, APC, Mfd15, D2S123, D18S69 and TP53Alu. A special embodiment has proven to be particularly advantageous in which primer pairs are selected from a group of primers represented by SEQ ID NOs. 1, 2, 5, 6, 19, 20, 27, 28, 31, 32, 33, 34, 35, 36, 45 and 46 for the analysis of 5 of these loci.

In a special embodiment the 5 loci BAT26, BAT40, APC, Mfd15 and D2S123 are analysed. In this case 1 or several primer pairs corresponding to SEQ ID NO. 1, 2, 5, 6, 19, 20, 33, 34, 35, 36 can be used.

In a further special embodiment the 5 loci BAT25, BAT26, APC, Mfd15 and D2S123 are analysed. In this case 1 or several primer pairs corresponding to SEQ ID NOs. 1, 2, 5, 6, 19, 20, 31, 32, 33, 34 can be used.

A further subject matter of the invention is the application of this method to the determination of the RER phenotype characterized in that when microsatellite instability is not detected at all 5 examined loci a RER− phenotype is assumed and when microsatellite. instability is detected at more than one locus an RER+ phenotype is assumed.

A particular embodiment is the application of the method to the prognostic diagnosis of tumours preferably of tumours of the endometrium, the gastrointestinal tract and in particular colorectal tumours.

Another special embodiment of the invention is the application of the method to the diagnosis of a familial tumour predisposition preferably for tumours of the endometrium, the gastrointestinal tract and in particular for colorectal tumours.

A further special embodiment of the invention is the application of the method to the early detection of tumours by detecting microsatellite instability in disseminated tumour cells.

An additional embodiment of the invention is the application of the method before deciding which type of chemotherapy should be used for a patient. This is important since chemotherapies are often associated with undesired side-effects so that an ineffective use of such a therapeutic for particular types of tumours should be avoided if possible.

A further subject matter of the invention is a kit for the tumour diagnostic analysis of microsatellite instability comprising at least 5 primer pairs which are suitable for the DNA amplification of two mononucleotide repeat loci, one or two dinucleotide repeat loci of class 2a, one or two dinucleotide repeat loci of class 2b and 0 to 1 pentanucleotide repeat locus.

A particular embodiment of the kit comprises at least 5 primer pairs which are suitable for the amplification of 5 loci selected from a group comprising BAT25, BAT26, BAT40, APC, Mfd15, D2S123, D18S69 and TP53Alu. These primers preferably have sequences according to SEQ ID NO: 1, 2, 5, 6, 19, 20, 27, 28, 31, 32, 33, 34, 35, 36, 45 and 46.

A special embodiment of the kit comprises at least 5 primer pairs for the analysis of BAT26, BAT40, APC, Mfd15 and D2S123. In this case one or several primer pairs can have sequences corresponding to SEQ ID NO. 1, 2, 5, 6, 19, 20, 33, 34, 35, 36 . . . .

In addition to the 5 primer pairs these kits can contain further primer pairs and molecular biological reagents and materials which serve to carry out MIN analyses according to the invention.

Different biological materials can be analysed as a source for isolating genomic DNA depending on the objective. Tumour tissue taken from the patient is used for a prognostic diagnosis as well as for the diagnosis of familial predisposition. When the method according to the invention is used for the early detection of tumours by the detection of MIN in disseminated tumour cells the DNA is isolated from body fluids or body secretions containing cellular components such as for example blood, serum, plasma, urine or faeces.

As a rule a control reaction is carried out with a DNA the sequence of which corresponds to the "healthy" wild type of the microsatellite locus to be analysed. Genomic DNA which has been isolated from healthy non-tumorigenic tissue of the same individual is particularly suitable.

Genomic DNA is isolated from formalin-stained tissue that is embedded in paraffin as follows:

prepare 5 µm sections with a microtome, mount on a microscope slide deparaffination: incubate the microscope slide at 65° C., 1 hour "draw through" an alcohol series: 2×15 min in xylol 2×15 min in EtOH(abs.) 2×15 min in EtOH(96%) 2×15 min in EtOH(70%) (storable for several weeks in 70% EtOH)

transfer the microscope slide to water scratch off the tissue in a wet state with a scalpel, glass capillary etc (microdissection), transfer to a 0.5 ml reaction vessel add 20–50 µl digestion buffer: 50 mM Tris-HCl, pH 7.5 5% Tween 20 1 mM EDTA add 7–15 µl proteinase K (20 mg/ml) (corresponds to 30–50% of the given volume)

incubate at 50° C. in a thermoblock with a heated cover until the solution is clear (overnight)

inactivate the proteinase K: 15 min at 94° C.

Optionally the DNA can be further purified with the Quiagen tissue DNA kit from the Quiagen company.

For the analysis of the biological material the PCR mixtures were pipetted together according to the following scheme:

| | Master mix for 1 reaction | | |
|---|---|---|---|
| | µl | final conc. | stock solution |
| H2O | 37.25 | | |
| DMSO | 2.5 | 5% | 100% |
| 10 x Expand-HiFi-buffer (BM) | 5 | 1 x | 10 x |
| dNTPs | 1.0 | 0.2 mM | 10 mM |

-continued

| | µl | final conc. | stock solution |
|---|---|---|---|
| Master mix for 1 reaction | | | |
| primer 1: | 1.0 | 0.3 µM | 15 µM |
| primer 2: | 1.0 | 0.3 µM | 15 µM |
| Taq-pol. Expand | 0.25 | 1.25 U | 5 U |
| HiFi-pol (BM) | | | |
| total | 48 | | |
| add: | 48 µl react mix to 2 µl template DNA | | |

As an alternative 2 or several loci were also analysed together in one reaction mixture in a duplex or multiplex analysis if fragment sizes were expected which differ considerably from one another. For this 2 or several primer pairs were used at the same final concentration of 0.3 µM per primer.

The PCR amplifications were carried out under standard conditions with 100 ng purified genomic DNA in a MJ Research thermocycler (PTC100, MJ Research, Watertown, Mass.) with the following cycles:

```
94° C. 3 min (single denaturation)
35 cycles:
94° C. 1 min
annealing temperature 50–68° C., 1 min
  corresponding to FIG. 1
72° C. 1 min
72° C. 8 min
```

The PCR products were subsequently separated for about one hour at 1800 volts and 55° C. on a denaturing 6.7% polyacrylamide gel containing 50% urea in a SequiGen sequence gel chamber (BioRad, Hercules, Calif.) and stained with silver nitrate (Budowle et al., (1991) Am. J. Hum. Genet., 48, 137–144) in a modified staining bath (Bender et al., (1994) Biotechniques, 16, 204–206) (Schlegl et al., (1995) Virchows Archiv, 426: 223–227).

Polyacrylamide Gel Electrophoresis to Separate the PCR Bands (6.7% PA-6M Urea Gel, Vertical Apparatus, Sequi-GenGT, BioRad)

3 µl PCR product

3 µl loading buffer (10 ml formamide 10 mg xylene cyanol 10 mg bromophenol blue 200 µl EDTA, 0.5 M)

denaturation, 94° C., 5 min 15 min PA initial gel pre-run at 2300 V (until 55° C. is reached)

loading the PA gel

45–75 min running time at 1800 V, 55° C.

Detection of the Separated PCR Products by Silver Staining remove the heat exchanger plate from the PA gel (between the heat exchanger plate and the glass plate) and place the Plexiglass staining frame on the PA gel (adhering to the glass plate) and fix with clips.

| * add the following solutions: | |
|---|---|
| H₂O | rinse briefly |
| 10% ethanol | 10 min |
| 1% nitric acid | 3 min |

| * add the following solutions: | |
|---|---|
| H₂O | rinse |
| 0.012 M silver nitrate | 20 min |
| H₂O | rinse |
| 0.28 M NaCO₃/0.019% formalin | rinse |
| 0.28 M NaCO₃/0.019% formalin | 3–6 min (until bands are visible) |
| 10% acetic acid | 3 min |
| H₂O | 3 min | remove the staining frame place Whatmann 3MM paper on the PA gel and use this to remove the PA gel from the glass plate cover the PA gel with clingfilm and dry for 1 hour in a gel dryer (GelDrying System, Biorad) (gels treated in this manner can be stored for an almost unlimited period).

25 different MIS loci on the DNA from 27 patients with colorectal carcinoma were examined for MIN. The selected patient group was pre-selected from a group of 200 patients in which 5 MIS loci had been analysed in an earlier prospective study (APC, D9S171, TP 53, D13S175, D11S904). In these 27 patients MIN had been detected at at least two loci in 5 cases, 5 further cases exhibited instability at one locus and had to be therefore classified as "low MIN+".

No instability was detectable in 17 cases. Additionally an MIS-stable cell line (SW480) and a cell line with the RER+ phenotype (HCT116) which had a defect in the hMSH2 mismatch repair gene were compared with the tumour material.

The MIS analysis was extended to a total of 25 MIS loci for a detailed analysis of the MIN status of these tumours. Representatives of all six different repeat types were analysed: 3 mononucleotide repeat loci (BAT25, BAT26, BAT40), 6 CA dinucleotide repeats of the class 2a (APC, D13S175, D3S1283, Mfd26, Mfd28 and Mfd41), 8 dinucleotide repeats of the class 2b (Mfd15, D10S197, D11S1318, D11S904, D18S69, D2S123, D9S171, TP53PCR), two loci with trinucleotide repeats. (AR, TBP), three loci with tetranucleotide repeats (HPRT, MYCL1, RB) and two loci with pentanucleotide repeats (FMR2, TP53alu). The exact sequences of these repeats were either taken from the gene library database or checked by directly sequencing PCR products. FIG. 1 gives an overview of the analysed loci as well as the primers used for each of the amplifications, the sequences of which are shown in SEQ ID NO. 1–50. FIG. 2a shows an example of amplifications of different alleles of all 25 examined gene loci. FIG. 2b shows an example of a duplex analysis of the loci BAT40 and D2S1283. If a loss of alleles occurred by tumour-dependent loss of heterozygosity (loss of heterozygosity, LOH (LiMao et al., (1996), Science, 271, 659–662) the result of the respective PCR was not taken into consideration in this study.

Identification of RER+ Tumours

In order to clarify which tumours can definitely be classified as RER+ and in order to examine whether some tumours have to be classified as "weak RER+", various tumours were compared with each other. According to the state of the art there is at present no simple method according to the "either or" principle for the unequivocal classification of a tumour as RER+ or RER−. The preselected group of 27 colorectal tumour patients, of which 17 were originally diagnosed as RER−, 5 as RER+ and 5 as "low MIN+", yielded a considerably more differentiated picture with regard to the distribution of MIN after analysis of further loci.

As shown in FIGS. 3 and 4a it was possible to detect 3 tumours with a MIN rate of more than 50% (14 MIN/24 loci, No. 1, 8 and 16), one tumour with 42% (10 MIN/24 loci, No. 5), one tumour with 38% (9 MIN/24 loci, No.2) and one tumour with 29% (7 MIN/24 loci, No.13). Thus all these tumours have the common feature of an instability frequency of more than 25% of the analysed loci. Hence this total of 6/27 tumours were classified unequivocally as RER+.

Furthermore 8 additional tumours were identified which had 1 to 2 MIN events (n=8, MIN frequency≦8%) and were therefore classified as "lowMIN+". In comparison to the earlier study in which only 5 instead of 25 MIS loci were analysed, the new study enables 13 instead of previously 17 cases to be classified as RER−. Thus this result achieved by extending the analysis to 25 MIS loci differs fundamentally from earlier studies according to the state of the art and illustrates the problem of an unreliable RER classification when a small number of MIS loci are arbitrarily selected for such a classification. However, in this connection it is of particular importance that it was not possible to detect any tumour with an average instability at 3 to 6 loci corresponding to a percentage of 10–25% so that an RER+ classification can be unequivocally made at a MIN rate above 25%.
Different MIS Loci Have Different MIN Frequencies Overall microsatellites were affected by instability in 14 of the 27 examined tumours. As expected MIN occurred more frequently in some tumours; however, individual MIN events were additionally also detected in other tumours. In order to determine whether MIN frequency depends on the repeat type, the MIN frequencies were determined separately for each repeat type and compared with the average MIN frequency of the entirety of the tested microsatellites: The average MIN rate relative to all loci examined per patient was 11.4% (78 MINs/25 loci=3.1 MIN/locus; average MIN rate=3.1/27 patients=11.4%). In contrast the average frequencies within the individual repeat types were different: all mononucleotide repeats were altered more frequently than average (5.0 MINs/27 patients=18.5%=+7.1%); all other repeat types were less frequently affected than the mononucleotide repeats. The MIN rates of complex dinucleotide loci as well as of non-complex dinucleotide loci did not differ significantly from the average determined for the entirety of all loci (0.3 and 0.9%). This applies similarly to the tetranucleotide repeats (+1.4%) which, however, have a pronounced heterogeneity with regard to each individual locus (−11.4% to +14.5%). An increased MIN frequency was determined for both trinucleotide repeats (+3.4%). In contrast pentanucleotide repeats had above average MIN frequencies (−4.0%). No MIN at all was detected at one locus of this type (FMR2). It follows that the determination of the frequency of MIN events is dramatically dependent on the selection of the analysed loci.
Certain MIS Loci are More Frequently Specifically Altered in RER+ Tumours Therefore for the analysis of the MIN status it is important whether there are certain loci that are specifically and regularly affected by MIN in RER+ tumours. In this respect a uniform result for MIS was only achieved with mononucleotide repeats (BAT25, BAT26, BAT40). Each of these loci was altered in the same 5 RER+ tumours (Nos. 1, 2, 8, 13, 16) but none had MIN in RER− tumours or "low MIN" tumours. In contrast all other tested loci except for Mfd15 were either mutated less often in the RER+ tumours or additionally altered in "low MIN" tumours. For example in the case of the APC locus it was possible to detect MIS not only in all RER+ tumours but also in tumour No. 20. Five loci exhibited MINs in 4/6 RER+ tumours but only D2S123 was unaltered in non-RER+ tumours. In contrast locus MYCL1, which was also altered in 4/6 RER+ tumours, exhibited additional instabilities in 3 "low MIN" tumours so that this locus is for example unsuitable as a marker.

Therefore a limitation to 5 markers for the analysis of microsatellite instability requires a specific selection of the loci so that it can nevertheless be ensured that the number of lowMIN+ cases that cannot be unequivocally classified is minimized and that all RER+ carriers can be identified with the highest possible degree of probability.

SHORT DESCRIPTION OF THE FIGURES

FIG. 1 shows a table of the most important features of the analysed MIS loci (locus symbol, marker name, chromosomal location, repeat type) and the parameters for the respective PCR amplification (PCR-Tm: hybridization temperature).

FIG. 2a shows the gel electrophoretic analysis of 25 examined microsatellite loci. The various alleles of the loci BAT26, BAT40, APC, MfD15, D2S123 and TP53Alu to be analysed according to the invention can be clearly distinguished from one another. FIG. 2b shows an example of a duplex analysis of the loci BAT40 and D3S1283 in one reaction mixture.

FIG. 3 shows the result of the study carried out in an overview. 27 Patients with colorectal tumours were examined at 25 different alleles for MIN. The result shows that (i) different MIS are affected by polymorphic changes at different frequencies and (ii) in different patients different classes of microsatellites are affected at different frequencies of genomic instability.

FIG. 4 classifies the tumours from the examined patient group of 27 persons according to the number of MIN events determined.

FIG. 4a shows the evaluation of all 25 MIS. The distribution shows that there is one group of 6 patients in which MIN occurs more frequently than 7 times so that this class can be unambiguously classified as the phenotype RER+. Furthermore there is a group of 8 patients in which 1 or 2 MIN were detected and which can thus be classified as "lowMIN+".

FIG. 4b shows the analysis according to the invention of 5 selected MIS as described in example 1. This analysis also leads to a distribution on the basis of which it is possible to make an unambiguous decision about the RER+ phenotype. Only 2 patients (No. 7, TP53Alu locus and No. 20, APC locus) had to be classified as low MIN+ according to this procedure.

FIG. 5 shows the date of birth, age and clinical data for the examined patient group, as of August 1994. (T, N, M: tumour classification, G: grade, LOC: tumour location, ri: colon right, le: colon left, R. rectum).

The invention is further elucidated by the following examples:

EXAMPLE 1

Selection of 2 Mononucleotide Repeat Loci, 1 Dinucleotide Repeat Locus of the Class 2a, 1 Dinucleotide Locus of the Class 2b and 1 Pentanucleotide Repeat Locus As the study showed, there were no false positive results when using mononucleotide repeat loci to determine the RER+ phenotype so that an analysis of these loci appears to be particularly suitable. On the other hand it was not possible to detect all RER+ tumours by analysing mononucleotide repeat loci. Thus for example tumour No. 5 was unambiguously RER+ but was not unstable with regard to the loci BAT25, BAT26 and BAT40 although it was possible to detect MIN at 9 loci with other repeat types. It was therefore necessary to select a combination of various repeat types for the most exact possible determination of the RER phenotype with a limited number of 5 analysed loci. This ensures that, despite the low number of analysed loci, on the one hand all RER+ carriers can be identified with the highest possible degree of probability and on the other hand the number of lowMIN+ cases that cannot be unambiguously classified is minimized as much as possible.

On the basis of the frequencies determined by the study with 27 tumours, the following criteria were laid down for the determination of the phenotype: in the case of at least 2 MIS-positive loci an RER+ phenotype should be assumed, if there is no positive detection of MIS an RER− phenotype should be assumed. The detection of exactly one MIN event was defined as "lowMIN+". (In ambiguous cases the latter requires the analysis of further MIS loci).

Figure 2A:
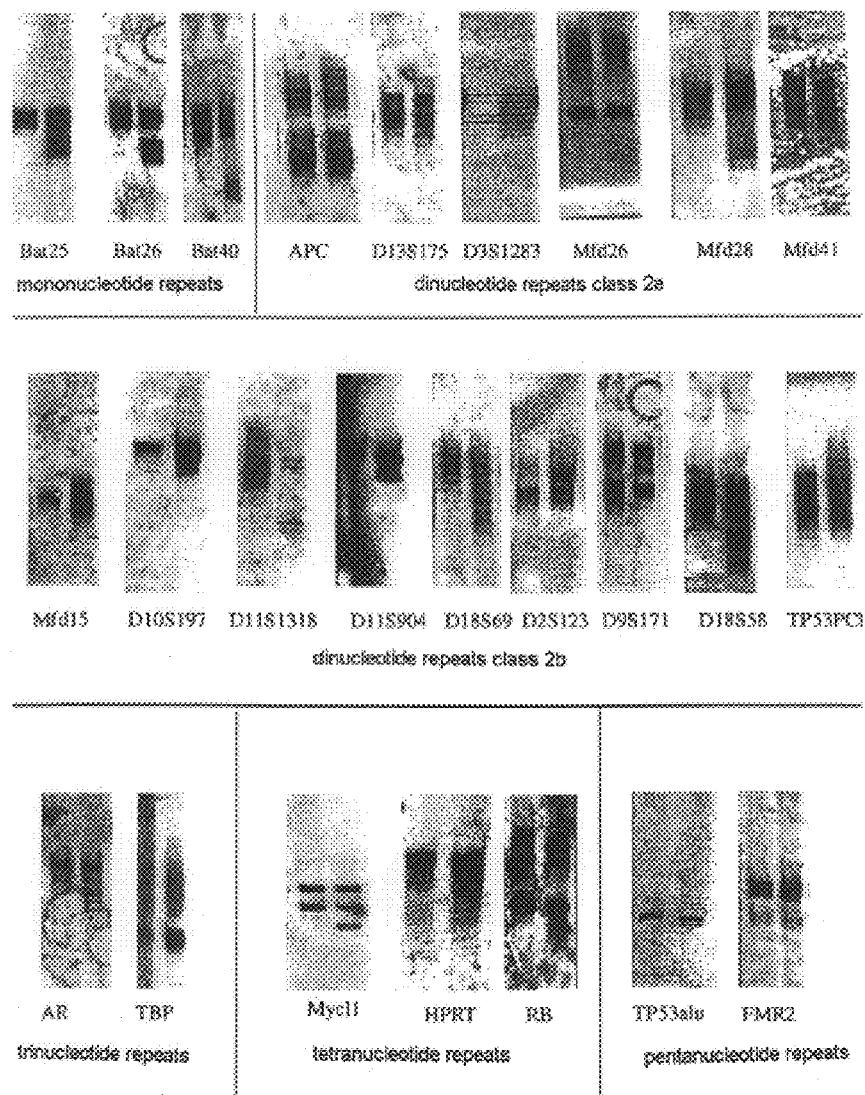
Figure 2B:
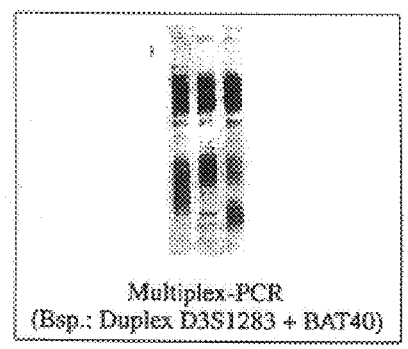
Figure 3:
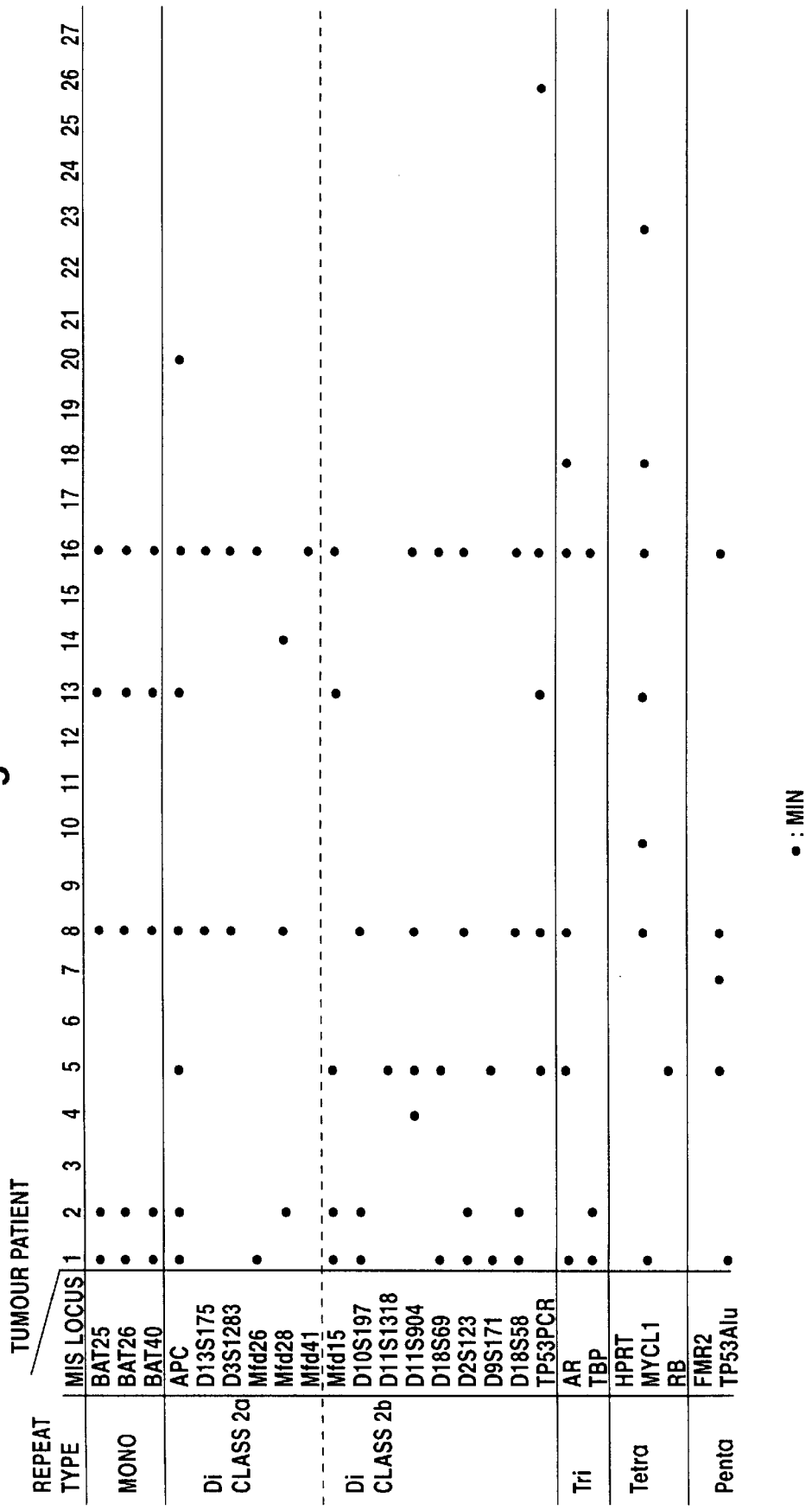
Figure 4A:
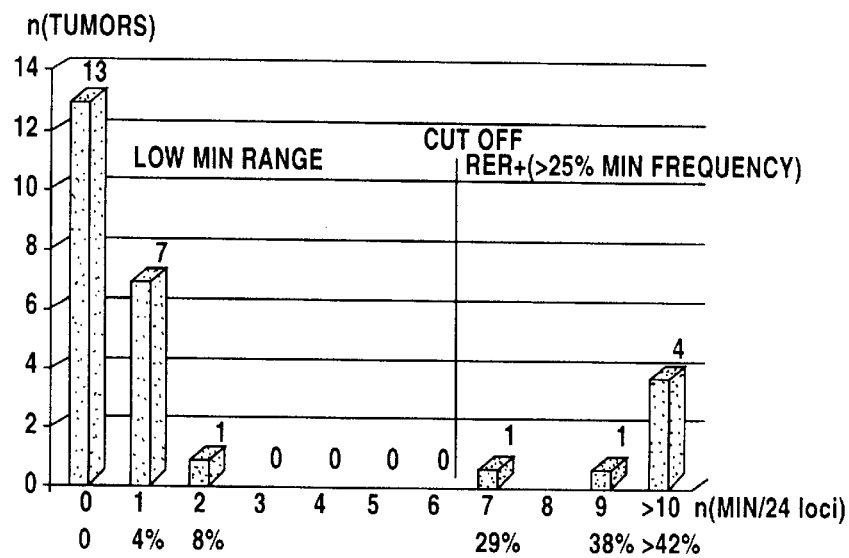
FIG. 4c shows the analysis of another selection according to the invention of 5 MIS according to example 2 which also enabled an unambiguous classification of the RER phenotype with one exception (APC, patient 20).
Figure 4B:
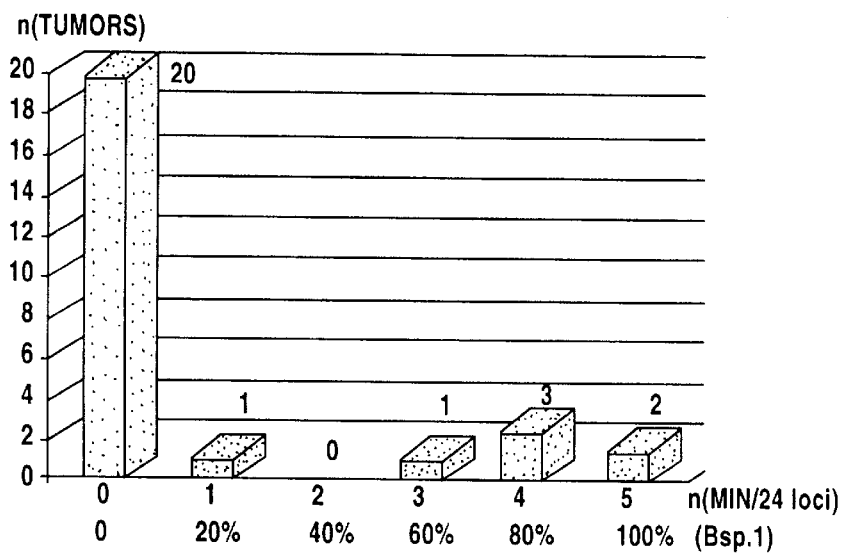

The evaluation of the 27 tumours by this procedure with respect to the loci BAT26, BAT40, APC, Mfd15, TP53Alu selected according to the invention led to the result shown in FIG. 4b. A frequency of at least three MIN events was determined for all 6 tumours which had been classified as RER+ by the analysis of 25 loci. Hence these tumours were also classified as RER+ by the analysis of the 5 selected loci. Only two tumours (No. 7, No. 20) were classified by this method as "lowMIN+" and cannot therefore be interpreted unambiguously.

EXAMPLE 2

Figure 4C:
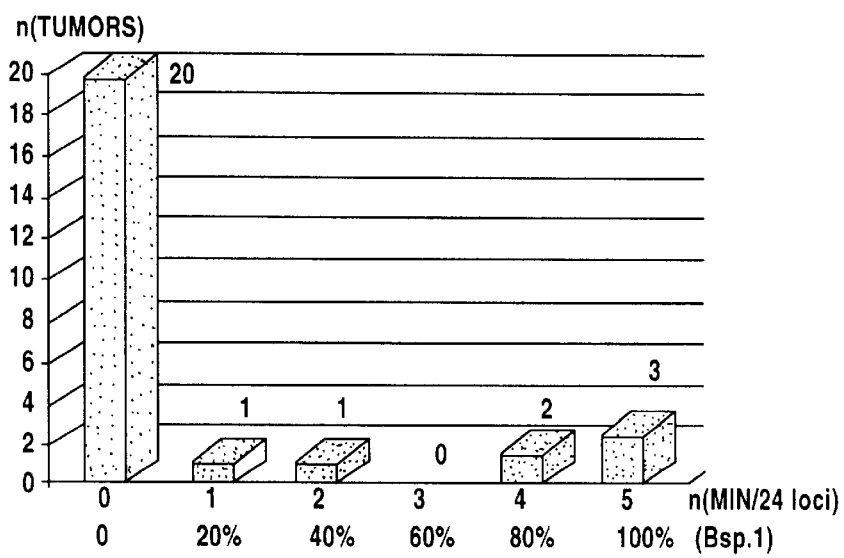

Selection of 2 Mononucleotide Repeat Loci, 1 Dinucleotide Repeat Locus of the Class 2a and 2 Dinucleotide Loci of the Class 2b The 27 tumours were evaluated by the same method as in example 1 but with a modified MIS selection that is also according to the invention (BAT26, BAT40, APC, Mfd15 and D18S69). The result is shown in FIG. 4c. At least three of the selected loci were altered in all tumours with the RER+ phenotype. Hence this selection of loci also enabled all six known RER+ tumours to be identified unambiguously as RER+. Only one tumour was classified in this case as "lowMIN+" and could therefore not be unambiguously interpreted.

EXAMPLE 3

Determination of the RER Phenotype as a Prognostic Indicator

In order to test the suitability of a selection according to the invention of 5 loci to determine the RER phenotype the clinical data tabulated in FIG. 5 were compared with the results of the MIN analysis from example 1. As disclosed in this example the analysis of the tested loci led to the detection of RER+ in 6 of a total of 27 examined tumour patients. Only 2 out of 6 (33%) of these RER+ patients were deceased at the conclusion of the study. Both were over 80 years old at this time. In contrast already 8 out of 19 (42%) of the patients classified as RER− in example 1 were deceased. Their average age at the time of the study was 64 years. Hence it is apparent that an analysis according to the invention of 5 microsatellite loci enabled a prognostic diagnosis about the course of the tumour disease.

We claim:

1. A method for determining the sizes of at least 5 different microsatellite loci comprising the following steps:
   (a) isolating genomic DNA from a biological sample of a mammal to obtain genomic DNA;
   (b) amplifying the genomic DNA of at least 5 different microsatellite loci to obtain DNA amplification products, wherein at least 2 loci of said 5 different microsatellite loci are mononucleotide repeat loci and the remaining loci of said 5 microsatellite loci are
      (i) one or two dinucleotide repeat loci of class 2a,
      (ii) one or two dinucleotide repeat loci of class 2b, and
      (iii) zero or one pentanucleotide repeat locus, wherein said pentanucleotide repeat locus is TP53Alu,
   with the proviso that the DNA of APC and at least one dinucleotide repeat locus of class 2b are amplified; and thereafter
   (c) determining the sizes of the DNA amplification products of step (b), wherein the sizes of the DNA amplification products of step (b) are indicative of the sizes of said at least 5 different microsatellite loci.

2. The method of claim 1, wherein 2 loci of said 5 different microsatellite loci are mononucleotide repeat loci and the remaining 3 loci of said 5 microsatellite loci are
   (i) APC, and
   (ii) two dinucleotide repeat loci of class 2b.

3. The method of claim 2 wherein said mammal is a human.

4. A method for determining the sizes of 5 microsatellite loci comprising the following steps:
   (a) obtaining genomic DNA from a biological sample of a mammal;
   (b) amplifying the genomic DNA of said 5 microsatellite loci using 5 different primer pairs to obtain DNA amplification products, wherein 2 loci of said 5 microsatellite loci are mononucleotide repeat loci and the remaining 3 loci of said 5 microsatellite loci are
      (i) one or two dinucleotide repeat loci of class 2a,
      (ii) one or two dinucleotide repeat loci of class 2b and
      (iii) zero or one pentanucleotide repeat locus, wherein said pentanucleotide repeat locus is TP53Alu,
   wherein the 2 mononucleotide repeat loci are selected from the group of loci consisting of BAT25, BAT26 and BAT40 and the remaining 3 loci of said 5 microsatellite loci are selected from the group of loci consisting of APC, Mfd15, D2S123, D18S69 and TP53A1u; and thereafter
   (c) determining the sizes of the DNA amplification products of step (b), wherein the sizes of the DNA amplification products of step (b) are indicative of the sizes of said 5 microsatellite loci.

5. The method of claim 4 wherein said 5 different primer pairs in step (b) are 2 primer pairs selected from a primer pair having the nucleotide sequences of SEQ ID NO: 31 and 32; a primer pair having the nucleotide sequences of SEQ ID NO: 33 and 34; and a primer pair having the nucleotide sequences of SEQ ID NO: 35 and 36, with the remainder of said 5 different primer pairs selected from a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; a primer pair having the nucleotide sequences of SEQ ID NO: 27 and 28; and a primer pair having the nucleotide sequences of SEQ ID NO: 45 and 46.

6. The method of claim 4 wherein the 5 different microsatellite loci are BAT26, BAT40, APC, Mfd15 and D2S123.

7. The method of claim 4 wherein the 5 different microsatellite loci are BAT25, BAT26, APC, Mfd15 and D2S123.

8. The method of claim 6 wherein said 5 different primer pairs are a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; a primer pair having the nucleotide sequences of SEQ ID NO: 33 and 34; and a primer pair having the nucleotide sequences of SEQ ID NO: 35 and 36.

9. The method of claim 7 wherein said 5 different primer pairs are a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; a primer pair having the nucleotide sequences of SEQ ID NO: 31 and 32; and a primer pair having the nucleotide sequences of SEQ ID NO: 33 and 34.

10. A method for determining microsatellite instability at any of 5 microsatellite loci in a target tissue of a mammal comprising the following steps:
    (A) conducting the method of claim 1 on a biological sample of said target tissue of the mammal to determine the sizes of amplification products produced thereby;
    (B) conducting the method of claim 1 on a biological sample of a normal tissue other than said target tissue of said mammal to determine the sizes of amplification products produced thereby; and thereafter
    (C) comparing the sizes obtained in step (A) with the sizes obtained in step (B) at the same microsatellite loci, wherein any difference between the size of the amplification product obtained in step (A) and the size of the amplification product obtained in step (B) indicates microsatellite instability of said any of 5 microsatellite loci in the target tissue.

11. The method of claim 10 wherein said mammal is a human.

12. A method for determining microsatellite instability at any of 5 microsatellite loci in a target tissue of a human comprising the following steps:
    (A) conducting the method of claim 5 on a biological sample of said target tissue of said human to obtain the sizes of amplification products produced thereby;

(B) conducting the method of claim 5 on a biological sample of a normal tissue other than said target tissue of said human to obtain the sizes of amplification products produced thereby; and thereafter (C) comparing the sizes obtained in step (A) with the sizes obtained in step (B) at the same loci, wherein any difference between the size of the amplification product of said any of 5 microsatellite loci obtained in step (A) and the size of the amplification product of the same microsatellite locus obtained in step (B) indicates microsatellite instability of said any of 5 microsatellite loci in the target tissue.

13. A method for determining microsatellite instability at any of 5 microsatellite loci in a target tissue of a human comprising the following steps:

(A) conducting the method of claim 8 on a biological sample of said target tissue of said human to obtain the sizes of amplification products produced thereby;

(B) conducting the method of claim 8 on a biological sample of a normal tissue of said human to obtain the sizes of amplification products produced thereby; and thereafter (C) comparing the sizes obtained in step (A) with the sizes obtained in step (B) at the same loci, wherein any difference between the size of the amplification product of said any of 5 microsatellite loci obtained in step (A) and the size of the amplification product of the same microsatellite locus obtained in step (B) indicates microsatellite instability of said any of 5 microsatellite loci in the target tissue.

14. A method for determining microsatellite instability at any of 5 microsatellite loci in a target tissue of a human comprising the following steps:

(A) conducting the method of claim 9 on a biological sample of said target tissue of said human to obtain the sizes of amplification products produced thereby;

(B) conducting the method of claim 9 on a biological sample of the normal tissue of said human to obtain the sizes of amplification products produced thereby; and thereafter (C) comparing the sizes obtained in step (A) with the sizes obtained in step (B) at the same loci, wherein any difference between the size of the amplification product of a microsatellite locus obtained in step (A) and the size of the amplification product of the same microsatellite locus obtained in step (B) indicates microsatellite instability of the microsatellite locus in the target tissue.

15. A method for determining an RER phenotype of a target tissue in a mammal by performing the method of claim 10 on the target tissue, wherein an RER– phenotype is assumed when no microsatellite instability is detected at all 5 microsatellite loci examined in step (b) and an RER+ phenotype is assumed when microsatellite instability is detected at a plurality of the 5 examined loci.

16. The method of claim 15, wherein said mammal is a human.

17. A method for determining an RER phenotype of a target tissue in a human by performing the method of claim 12 on the target tissue, wherein an RER– phenotype is assumed when no microsatellite instability is detected at all 5 microsatellite loci examined in step (b) and an RER+ phenotype is assumed when microsatellite instability is detected at a plurality of the 5 microsatellite loci examined in step (b).

18. A method for determining an RER phenotype of a target tissue in a human by performing the method of claim 13 on the target tissue, wherein an RER– phenotype is assumed when no microsatellite instability is detected at all 5 microsatellite loci examined in step (b) and an RER+ phenotype is assumed when microsatellite instability is detected at a plurality of the 5 microsatellite loci examined in step (b).

19. A method for determining an RER phenotype of a target tissue in a human by performing the method of claim 14 on the target tissue, wherein an RER– phenotype is assumed when no microsatellite in stability is detected at all 5 microsatellite loci examined in step (b) and an RER+ phenotype is assumed when microsatellite instability is detected at a plurality of the 5 microsatellite loci examined in step (b).

20. A method for determining the prognosis of a tumor of the gastrointestinal tract or endometrium in a human, by conducting the method of claim 15, with the tumor as the target tissue, to obtain the RER phenotype of the tumor with a RER+ phenotype indicating better prognosis than a RER– phenotype, wherein the 5 microsatellite loci examined are (I) two mononucleotide repeat loci, wherein said mononucleotide repeat loci are selected from BAT25, BAT26 and BAT40;

(II) one dinucleotide repeat locus of class 2a, wherein said dinucleotide repeat locus of class 2a is APC;

(III) one or two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected; and (IV) zero or one pentanucleotide repeat locus, wherein said pentanucleotide repeat locus is TP53Alu.

21. A method for determining the prognosis of a tumor in a human by conducting the method of claim 17 with the tumor as the target tissue, to obtain the RER phenotype of the tumor and using said RER phenotype so obtained as a prognostic indicator with a RER+ phenotype indicating better prognosis than a RER– phenotype, wherein the tumor is a gastrointestinal tumor or endometrial tumor.

22. A method for determining the prognosis of a tumor in a human by conducting the method of claim 18 with the tumor as the target tissue, to obtain the RER phenotype of the tumor and using said RER phenotype so obtained as a prognostic indicator with a RER+ phenotype indicating better prognosis than a RER– phenotype, wherein the tumor is a gastrointestinal tumor or endometrial tumor.

23. A method for determining the prognosis of a tumor in a human by conducting the method of claim 19, with the tumor as the target tissue, to obtain the RER phenotype of the tumor and using said RER phenotype so obtained as a prognostic indicator with a RER+ phenotype indicating better prognosis than a RER– phenotype, wherein the tumor is a gastrointestinal tumor or endometrial tumor.

24. A method for determining familial tumor predisposition in a human, said method comprises the following steps:

(a) isolating genomic DNA from a tumor of said human to obtain tumor genomic DNA, wherein the tumor is a gastrointestinal tumor or endometrial tumor;

(b) amplifying the tumor genomic DNA at 5 different microsatellite loci, wherein 2 loci of said 5 different microsatellite loci are mononucleotide repeat loci selected from BAT25, BAT26 and BAT40 and the remaining 3 loci of said 5 microsatellite loci are (i) one dinucleotide repeat locus of class 2a, wherein said dinucleotide repeat locus of class 2a is APC, (ii) one or two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected, and (iii) zero or one pentanucleotide repeat locus, wherein said pentanucleotide repeat locus is TP53Alu, to obtain tumor DNA amplification products;

(c) determining the sizes of the tumor DNA amplification products;

(d) isolating genomic DNA from a normal tissue of said human to obtain normal genomic DNA;

(e) amplifying the normal genomic DNA at said 5 different microsatellite loci to obtain normal DNA amplification products;

(f) determining the sizes of the normal DNA amplification products;

(g) comparing the sizes of the tumor DNA amplification products and the sizes of the normal DNA amplification products at the same microsatellite loci, wherein any difference between the size of the tumor DNA amplification product and the normal DNA amplification product for any of said 5 microsatellite loci indicates microsatellite instability of said any of said 5 microsatellite loci in said tumor;

(h) obtaining an RER phenotype for said tumor by assigning an RER+ phenotype when microsatellite instability is detected in a plurality of said 5 microsatellite loci and by assigning an RER− phenotype when no microsatellite instability is detected at said 5 microsatellite loci, and thereafter (h) using said RER phenotype so obtained as an indicator of familial tumor predisposition with a RER+ phenotype indicating familial tumor predisposition.

25. A method for determining familial tumor predisposition in a human by conducting the method of claim 17, with a tumor in said human as the target tissue, to obtain the RER phenotype of the tumor and using said RER phenotype so obtained as an indicator of familial tumor predisposition with a RER+ phenotype indicating familial tumor predisposition, wherein the tumor is a gastrointestinal tumor endometrial tumor.

26. A method for determining familial tumor predisposition in a human by conducting the method of claim 18 with a tumor in said human as the target tissue, to obtain the RER phenotype of the tumor and using said RER phenotype so obtained as an indicator of familial tumor predisposition with a RER+ phenotype indicating familial tumor predisposition, wherein the tumor is a gastrointestinal tumor or endometrial tumor.

27. A method for determining familial tumor predisposition in a human by conducting the method of claim 19 with a tumor in said human as the target tissue, to obtain the RER phenotype of the tumor and using said RER phenotype so obtained as an indicator of familial tumor predisposition with a RER+ phenotype indicating familial tumor predisposition, wherein the tumor is a gastrointestinal tumor or endometrial tumor.

28. The method of claim 24, wherein said tumor is a colorectal tumor.

29. The method of claim 25, wherein said tumor is a colorectal tumor.

30. The method of claim 26 wherein said tumor is a colorectal tumor.

31. The method of claim 27, wherein said tumor is a colorectal tumor.

32. A method for detecting a tumor of the gastrointestinal tract or endometrium in a human, said method comprises the following steps:

(a) isolating genomic DNA from a target tissue of said human to obtain target genomic DNA, wherein the target tissue is a gastrointestinal or endometrial tissue;

(b) amplifying the target genomic DNA at 5 different microsatellite loci, wherein 2 loci of said 5 different microsatellite loci are mononucleotide repeat loci selected from BAT25, BAT26 and BAT40 and the remaining 3 loci of said 5 microsatellite loci are (i) one dinucleotide repeat locus of class 2a, wherein said dinucleotide repeat locus of class 2a is APC, (ii) one or two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected, and (iii) zero or one pentanucleotide repeat locus, wherein said pentanucleotide repeat locus is TP53Alu, to obtain target DNA amplification products;

(c) determining the sizes of the target DNA amplification products;

(d) isolating genomic DNA from a tissue, other than said target tissue, of said human to obtain non-target genomic DNA;

(e) amplifying the non-target genomic DNA at said 5 different microsatellite loci to obtain non-target DNA amplification products;

(f) determining the sizes of the non-target DNA amplification products;

(g) comparing the sizes of the target DNA amplification products and the sizes of the non-target DNA amplification products at the same microsatellite loci, wherein any difference between the size of the target DNA amplification product and the non-target DNA amplification product for any of said 5 microsatellite loci indicates microsatellite instability of said any of said 5 microsatellite loci in said target tissue;

(h) obtaining an RER phenotype for said target tissue by assigning an RER+ phenotype when microsatellite instability is detected in a plurality of said 5 microsatellite loci and by assigning an RER− phenotype when no microsatellite instability is detected at said 5 microsatellite loci, and thereafter (h) using said RER phenotype so obtained as an indicator of the tumor in said target tissue with a RER+ phenotype indicating the presence of the tumor in said target tissue.

33. A method for detecting a tumor in a mammal, wherein said mammal is a human, by conducting the method of claim 17 on a target tissue of said human to obtain the RER phenotype of the target tissue and using said RER phenotype so obtained as an indicator of the tumor of said target tissue with a RER+ phenotype indicating the presence of the tumor of said target tissue, wherein the tumor is a gastrointestinal tumor or endometrial tumor, wherein the target tissue is a gastrointestinal or endometrial tissue.

34. A method for detecting a tumor in a mammal, wherein said mammal is a human, by conducting the method of claim 18 on a target tissue of said human to obtain the RER phenotype of the target tissue and using said RER phenotype so obtained as an indicator of the tumor of said target tissue with a RER+ phenotype indicating the presence of the tumor of said target tissue, wherein the tumor is a gastrointestinal tumor or endometrial tumor, wherein the target tissue is a gastrointestinal or endometrial tissue.

35. A method for detecting a tumor in a mammal, wherein said mammal is a human, by conducting the method of claim 19 on a target tissue of said mammal to obtain the RER phenotype of the target tissue and using said RER phenotype so obtained as an indicator of the tumor of said target tissue with a RER+ phenotype indicating the presence of the tumor of said target tissue, wherein the tumor is a gastrointestinal tumor or endometrial tumor, wherein the target tissue is a gastrointestinal or endometrial tissue.

36. A method for detecting a tumor of the gastrointestinal tract or endometrium in a human by conducting the method of claim 17 with a tissue of the gastrointestinal tract or endometrium as the target tissue, to obtain the RER phenotype of the target tissue and using said RER phenotype so obtained as an indicator of the tumor with a RER+ phenotype indicating the presence of the tumor of the gastrointestinal tract or endometrium.

37. A method for detecting a tumor of the gastrointestinal tract or endometrium in a human by conducting the method of claim 18 with a tissue of the gastrointestinal tract or endometrium as the target tissue, to obtain the RER phenotype of the target tissue and using said RER phenotype so obtained as an indicator of the tumor with a RER+ phenotype indicating the presence of the tumor of the gastrointestinal tract or endometrium.

38. A method for detecting a tumor of the gastrointestinal tract or endometrium in a human by conducting the method of claim 19, with a tissue of the gastrointestinal tract or endometrium as the target tissue, to obtain the RER phenotype of the target tissue and using said RER phenotype so obtained as an indicator of the tumor with a RER+ phenotype indicating the presence of the tumor of the gastrointestinal tract or endometrium.

39. The method according to claim 32 for detecting a colorectal tumor, wherein said target tissue is a colorectal tissue.

40. A method for detecting a colorectal tumor in a human by conducting the method of claim 17, with a colorectal tissue as the target tissue, to obtain the RER phenotype and using said RER phenotype so obtained as an indicator of the colorectal tumor with a RER+ phenotype indicating the presence of the colorectal tumor.

41. A method for detecting a colorectal tumor in a human by conducting the method of claim 18, with a colorectal tissue as the target tissue, to obtain the RER phenotype and using said RER phenotype so obtained as an indicator of the colorectal tumor with a RER+ phenotype indicating the presence of the colorectal tumor.

42. A method for detecting a colorectal tumor in a human by conducting the method of claim 19, with a colorectal tissue as the target tissue, to obtain the RER phenotype and using said RER phenotype so obtained as an indicator of the colorectal tumor with a RER+ phenotype indicating the presence of the colorectal tumor.

43. A method for early detection of a tumor of the gastrointestinal tract or endometrium in a human, said method comprising the following steps:
  (a) isolating genomic DNA from disseminated tumor cells obtained from said human to obtain tumor genomic DNA;
  (b) amplifying the tumor genomic DNA at 5 different microsatellite loci, wherein 2 loci of said 5 different microsatellite loci are mononucleotide repeat loci selected from BAT25, BAT26 and BAT40 and the remaining 3 loci of said 5 microsatellite loci are
    (i) one dinucleotide repeat locus of class 2a, wherein said dinucleotide repeat locus of class 2a is APC,
    (ii) one or two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected and
    (iii) zero or one pentanucleotide repeat locus, wherein said pentanucleotide repeat locus is TP53Alu,
  to obtain tumor DNA amplification products;
  (c) determining the sizes of the tumor DNA amplification products;
  (d) isolating genomic DNA from a non-tumor tissue of said human to obtain non-tumor genomic DNA;
  (e) amplifying the non-tumor genomic DNA at said 5 different microsatellite loci to obtain non-tumor DNA amplification products;
  (f) determining the sizes of the non-tumor DNA amplification products; and thereafter
  (g) comparing the sizes of the tumor DNA amplification products and the sizes of the non-tumor DNA amplification products at the same microsatellite loci, wherein any difference between the size of the tumor DNA amplification product and the non-tumor DNA amplification product for any of said 5 microsatellite loci indicates microsatellite instability of said any of said 5 microsatellite loci in said tumor cells;
  wherein the microsatellite instability so obtained indicates the presence of the tumor of the gastrointestinal tract or endometrium allowing early detection of the tumor of the gastrointestinal tract or endometrium.

44. A method for early detection of a tumor of the gastrointestinal tract or endometrium in a human by conducting the method of claim 12 on disseminated tumor cells obtained from said human to determine microsatellite instability at the 5 microsatellite loci, wherein any microsatellite instability so obtained indicates the presence of the tumor of the gastrointestinal tract or endometrium allowing early detection of the tumor of the gastrointestinal tract or endometrium.

45. A method for early detection of a tumor of the gastrointestinal tract or endometrium in a human by conducting the method of claim 13 on disseminated tumor cells obtained from said human to determine microsatellite instability at the 5 microsatellite loci, wherein any microsatellite instability so obtained indicates the presence of the tumor of the gastrointestinal tract or endometrium allowing early detection of the tumor of the gastrointestinal tract or endometrium.

46. A method for early detection of a tumor of the gastrointestinal tract or endometrium in a human by conducting the method of claim 14 on disseminated tumor cells obtained from said human to determine microsatellite instability at the 5 microsatellite loci, wherein any microsatellite instability so obtained indicates the presence of the tumor of the gastrointestinal tract or endometrium allowing early detection of the tumor of the gastrointestinal tract or endometrium.

47. A kit consisting essentially of 5 different primer pairs wherein at least 2 of said 5 different primer pairs are suitable for DNA amplification of mononucleotide repeat loci and the remaining primer pairs of said 5 different primer pairs are suitable for the DNA amplification of
  (i) one or two dinucleotide repeat loci of class 2a,
  (ii) one or two dinucleotide repeat loci of class 2b and
  (iii) zero or one pentanucleotide repeat locus, wherein said pentanucleotide repeat locus is TP53Alu,
with the proviso that said kit contains a primer pair for APC and a primer pair for at least one dinucleotide repeat locus of class 2b.

48. The kit of claim 47, wherein 2 of said 5 different primer pairs are suitable for DNA amplification of mononucleotide repeat loci and the remaining 3 primer pairs of said 5 different primer pairs are suitable for the DNA amplification of
   (i) APC, and
   (ii) two dinucleotide repeat loci of class 2b.

49. The kit of claim 48, wherein said 2 of said 5 different primer pairs are suitable for DNA amplification of mononucleotide repeat loci selected from BAT25, BAT26 and BAT40, and the remaining 3 primer pairs of said 5 different primer pairs are suitable for DNA amplification of repeat loci selected from APC, Mfd15, D2S123, and D18S69.

50. The kit of claim 49, wherein said 5 different primer pairs are primer pairs suitable for DNA amplification of BAT26, BAT40, APC, Mfd15 and D2S123.

51. The kit of claim 49, wherein said 5 different primer pairs are primer suitable for DNA amplification of BAT25, BAT26, APC, Mdf15 and D2S123.

52. The kit of claim 49, wherein said 2 of said 5 different primer pairs are 2 primer pairs selected from a primer pair having the nucleotide sequences of SEQ ID NO: 31 and 32; a primer pair having the nucleotide sequences of SEQ ID NO: 33 and 34; and a primer pair having the nucleotide sequences of SEQ ID NO: 35 and 36 and said remaining 3 primer pairs of said 5 different primer pairs are selected from a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; and a primer pair having the nucleotide sequences of SEQ ID NO: 27 and 28.

53. The kit of claim 49 wherein said 5 different primer pairs are a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; a primer pair having the nucleotide sequences of SEQ ID NO: 33 and 34; and a primer pair having the nucleotide sequences of SEQ ID NO: 35 and 36.

54. The kit of claim 49, wherein said 5 different primer pairs are a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; a primer pair having the nucleotide sequences of SEQ ID NO: 31 and 32; and a primer pair having the nucleotide sequences of SEQ ID NO: 33 and 34.

55. A method for detecting a colorectal tumor in a human, comprising
   (a) obtaining genomic DNA from a sample of a colorectal target tissue of the human;
   (b) amplifying the genomic DNA of 5 different microsatellite loci using 5 different primer pairs, wherein 2 loci of said 5 different microsatellite loci are mononucleotide repeat loci selected from BAT25, BAT26 and BAT40 and the remaining 3 loci of said 5 different microsatellite loci are
      (i) one dinucleotide repeat locus of class 2a, wherein said dinucleotide repeat locus of class 2a is APC,
      (ii) one or two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected, and
      (iii) zero or one pentanucleotide repeat locus, wherein said pentanucleotide repeat locus is TP53Alu;
   (c) determining the sizes of the amplification products of step (b);
   (d) obtaining genomic DNA from a sample of a non-colorectal tissue of the human;
   (e) conducting steps (b) and (c) on the genomic DNA obtained from step (d) to determine the sizes of amplification products of the same 5 microsatellite loci examined in step (b);
   (f) comparing the sizes obtained in step (c) with the sizes obtained in step (e) at the same loci, wherein any difference between the size of the amplification product of a microsatellite locus obtained in step (c) and the size of the amplification product of the same microsatellite locus obtained in step (e) indicates microsatellite instability of the locus;
   (g) determining an RER phenotype of the colorectal target tissue by assuming an RER– phenotype when no microsatellite instability is detected at all 5 microsatellite loci and an RER+ phenotype when microsatellite instability is detected in a plurality of the 5 microsatellite loci; and thereafter
   (h) using said RER phenotype as an indicator of the colorectal tumor with a RER+ phenotype indicating the presence of the colorectal tumor.

56. The method of claim 55, wherein said dinucleotide repeat loci of class 2b are selected from Mfd15, D2S123 and D18S69, wherein at least one of Mfd15 and D18S69 is selected.

57. The method of claim 56, wherein said 5 different microsatellite loci are BAT26, BAT40, APC, Mfd15 and D2S123.

58. The method of 56, wherein said 5 different microsatellite loci are BAT25, BAT26, APC, Mfd15 and D2S123.

59. The method of claim 56, wherein primer pairs for said mononucleotide repeat loci are primer pairs selected from a primer pair having the nucleotide sequences of SEQ ID NO: 31 and 32; a primer pair having the nucleotide sequences of SEQ ID NO: 33 and 34; and a primer pair having the nucleotide sequences of SEQ ID NO: 35 and 36; wherein a primer pair for APC has the nucleotide sequences of SEQ ID NO: 1 and 2; and wherein primer pairs for said dinucleotide repeat loci of class 2b are selected from a primer pair having the nucleotide sequences of SEQ ID NO: 5 and 6; a primer pair having the nucleotide sequences of SEQ ID NO: 19 and 20; and a primer pair having the nucleotide sequences of SEQ ID NO: 27 and 28.

60. The method of claim 57 wherein said 5 different primer pairs are a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; a primer pair having the nucleotide sequences of SEQ ID NO: 33 and 34; and a primer pair having the nucleotide sequences of SEQ ID NO: 35 and 36.

61. The method of claim 58 wherein said 5 different primer pairs are a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; a primer pair having the nucleotide sequences of SEQ ID NO: 31 and 32; and a primer pair having the nucleotide sequences of SEQ ID NO: 33 and 34.

62. A method for determining the prognosis of a tumor in a mammal, wherein said mammal is a human, by conducting the method of claim 15, with the tumor as the target tissue, to obtain the RER phenotype of the tumor and using said RER phenotype so obtained as a prognostic indicator with a RER+ phenotype indicating better prognosis than a RER– phenotype, wherein the tumor is a gastrointestinal tumor or endometrial tumor, wherein the 5 microsatellite loci examined in step (b) are
- (I) two mononucleotide repeat loci, wherein said mononucleotide repeat loci are are selected from BAT25, BAT26 and BAT40;
- (II) one dinucleotide repeat locus of class 2a, wherein said dinucleotide repeat locus of class 2a is APC; and
- (III) two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected.

63. A method for detecting a tumor in a mammal by conducting the method of claim 15 on a target tissue of said mammal to obtain the RER phenotype of the target tissue and using said RER phenotype so obtained as an indicator of the tumor of said target tissue with a RER+ phenotype indicating the presence of the tumor in said target tissue, wherein said mammal is a human, wherein the tumor is a gastrointestinal tumor or endometrial tumor, wherein the target tissue is a gastrointestinal or endometrial tissue, wherein the 5 microsatellite loci examined in step (b) are
- (I) two mononucleotide repeat loci, wherein said mononucleotide repeat loci are are selected from BAT25, BAT26 and BAT40;
- (II) one dinucleotide repeat locus of class 2a, wherein said dinucleotide repeat locus of class 2a is APC; and
- (III) two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected.

64. A method for detecting a tumor of the gastrointestinal tract or endometrium in a mammal by conducting the method of claim 15, with a tissue of the gastrointestinal tract or endometrium as the target tissue, to obtain the RER phenotype of the target tissue and using said RER phenotype so obtained as an indicator of the tumor of the gastrointestinal tract or endometrium with a RER+ phenotype indicating the presence of the tumor of the gastrointestinal tract or endometrium, wherein said mammal is a human, wherein the 5 microsatellite loci examined in step (b) are
- (I) two mononucleotide repeat loci, wherein said mononucleotide repeat loci are selected from BAT25, BAT26 and BAT40;
- (II) one dinucleotide repeat locus of class 2a, wherein said dinucleotide repeat locus of class 2a is APC; and
- (III) two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected.

65. A method for detecting a colorectal tumor in a mammal by conducting the method of claim 15, with a colorectal tissue as the target tissue, to obtain the RER phenotype and using said RER phenotype so obtained as an indicator of the colorectal tumor with a RER+ phenotype indicating the presence of the colorectal tumor, wherein said mammal is a human, wherein the 5 microsatellite loci examined in step (b) are
- (I) two mononucleotide repeat loci, wherein said mononucleotide repeat loci are are selected from BAT25, BAT26 and BAT40;
- (II) one dinucleotide repeat locus of class 2a, wherein said dinucleotide repeat locus of class 2a is APC; and
- (III) two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected.

66. A method for detection of a tumor of the gastrointestinal tract or endometrium in a mammal by conducting the method of claim 10 on disseminated tumor cells obtained from said mammal to determine microsatellite instability at the 5 microsatellite loci, wherein said microsatellite instability indicates the presence of the tumor of the gastrointestinal tract or endometrium, wherein said mammal is a human, wherein the 5 microsatellite loci examined in step (b) are
- (I) two mononucleotide repeat loci, wherein said mononucleotide repeat loci are are selected from BAT25, BAT26 and BAT40;
- (II) one dinucleotide repeat locus of class 2a, wherein said dinucleotide repeat locus of class 2a is APC; and
- (III) two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected.

67. A method for determining the prognosis or the familial predisposition of a colorectal tumor in a human, comprising
- (a) obtaining genomic DNA from a sample of the colorectal tumor of the human;
- (b) amplifying the genomic DNA of 5 different microsatellite loci using 5 different primer pairs, wherein 2 loci of said 5 different microsatellite loci are mononucleotide repeat loci selected from BAT25, BAT26 and BAT40 and the remaining 3 loci of said 5 different microsatellite loci are
  - (i) one dinucleotide repeat locus of class 2a, wherein said dinucleotide repeat locus of class 2a is APC,
  - (ii) one or two dinucleotide repeat loci of class 2b, wherein the dinucleotide repeat loci of class 2b are selected from the group consisting of Mfd15, D2S123, D18S69, D10S197 and D18S58, wherein at least one of Mfd15 and D18S69 is selected, and
  - (iii) zero or one pentanucleotide repeat locus, wherein said pentanucleotide repeat locus is TP53Alu;
- (c) determining the sizes of the amplification products of step (b);
- (d) obtaining genomic DNA from a sample of a normal tissue of the human;
- (e) conducting steps (b) and (c) on the genomic DNA obtained from step (d) to determine the sizes of amplification products of the same 5 microsatellite loci examined in step (b);
- (f) comparing the sizes obtained in step (c) with the sizes obtained in step (e) at the same loci, wherein any difference between the size of the amplification product of a microsatellite locus obtained in step (c) and the size of the amplification product of the same microsatellite locus obtained in step (e) indicates microsatellite instability of the locus;
- (g) determining an RER phenotype of the colorectal tumor by assuming an RER− phenotype when no microsatellite instability is detected at all 5 microsatellite loci and an RER+ phenotype when microsatellite instability is detected in a plurality of the 5 microsatellite loci; and thereafter
- (h) using said RER phenotype as an indicator of the prognosis or familial predisposition of the colorectal tumor with a RER+ phenotype indicating better prognosis than a RER− phenotype or with a RER+ phenotype indicating familial predisposition of the colorectal tumor.

68. The method of claim 67, wherein said dinucleotide repeat loci of class 2b are selected from Mfd15, D2S123, and D18S69, wherein at least one of Mfd15 and D18S69 is selected.

69. The method of claim 68 wherein said 5 different microsatellite loci are BAT26, BAT40, APC, Mfd15 and D2S123.

70. The method of claim 68, wherein said 5 different microsatellite loci are BAT25, BAT26, APC, Mfd15 and D2S123.

71. The method of claim 68, wherein primer pairs for said mononucleotide repeat loci are primer pairs selected from a primer pair having the nucleotide sequences of SEQ ID NO: 31 and 32; a primer pair having the nucleotide sequences of SEQ ID NO: 33 and 34; and a primer pair having the nucleotide sequences of SEQ ID NO: 35 and 36; and wherein primer pairs for the remaining 3 loci are selected from a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; a primer pair having the nucleotide sequences of SEQ ID NO: 27 and 28; and a primer pair having the nucleotide sequences of SEQ ID NO: 45 and 46.

72. The method of claim 69, wherein said 5 different primer pairs are a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; a primer pair having the nucleotide sequences of SEQ ID NO: 33 and 34; and a primer pair having the nucleotide sequences of SEQ ID NO: 35 and 36.

73. The method of claim 70 wherein said 5 different primer pairs are a primer pair having the nucleotide sequences of SEQ ID NO: 1 and 2; a primer pair having the nucleotide sequences of SEQ ID NO: 5 and 6; a primer pair having the nucleotide sequences of SEQ ID NO: 19 and 20; a primer pair having the nucleotide sequences of SEQ ID NO: 31 and 32; and a primer pair having the nucleotide sequences of SEQ ID NO: 33 and 34.

* * * * *

SEQUENCE LISTING (1) GENERAL INFORMATION:

(iii) NUMBER OF SEQUENCES: 50

(2) INFORMATION FOR SEQ ID NO: 1:

(i) SEQUENCE CHARACTERISTICS:
      (A) LENGTH: 20 Base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

AAACAGGATG CCTGCCTTTA                                          20

(2) INFORMATION FOR SEQ ID NO: 2:

(i) SEQUENCE CHARACTERISTICS:
      (A) LENGTH: 20 Base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 2:

GGACTTTCCA CCTATGGGAC                                          20

(2) INFORMATION FOR SEQ ID NO: 3:

(i) SEQUENCE CHARACTERISTICS:
        (A) LENGTH: 22 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

GGCAGTACCA CCTGTAGAAA TG                                                    22

(2) INFORMATION FOR SEQ ID NO: 4:

(i) SEQUENCE CHARACTERISTICS:
        (A) LENGTH: 24 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

GAGTAACAGA GGCATCGTGT ATTC                                               24

(2) INFORMATION FOR SEQ ID NO: 5:

(i) SEQUENCE CHARACTERISTICS:
        (A) LENGTH: 21 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

ACTCACTCTA GTGATAAATC G                                                     21

(2) INFORMATION FOR SEQ ID NO: 6:

(i) SEQUENCE CHARACTERISTICS:
        (A) LENGTH: 25 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

AGCAGATAAG ACAGTATTAC TAGTT                                         25

(2) INFORMATION FOR SEQ ID NO: 7:

(i) SEQUENCE CHARACTERISTICS:
        (A) LENGTH: 25 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

AGCTAAGTGA ACCTCATCTC TGTCT                                         25

(2) INFORMATION FOR SEQ ID NO: 8:

(i) SEQUENCE CHARACTERISTICS:
        (A) LENGTH: 24 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

ACCCTAGCAC TGATGGTATA GTCT                                                  24

(2) INFORMATION FOR SEQ ID NO: 9:

(i) SEQUENCE CHARACTERISTICS:
        (A) LENGTH: 21 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

AACACTAGTG ACATTATTTT C                                                     21

(2) INFORMATION FOR SEQ ID NO: 10:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

AGCTAGGCCT GAAGGCTTCT                                                       20

(2) INFORMATION FOR SEQ ID NO: 11:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

ACCACTGCAC TTCAGGTGAC                                                       20

(2) INFORMATION FOR SEQ ID NO: 12:

(i) SEQUENCE CHARACTERISTICS:
        (A) LENGTH: 22 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

GTGATACTGT CCTCAGGTCT CC                                                    22

(2) INFORMATION FOR SEQ ID NO: 13:

(i) SEQUENCE CHARACTERISTICS:
        (A) LENGTH: 20 Base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO: 13:

ATGACAAGCA ATCCTTGAGC                                                   20

(2) INFORMATION FOR SEQ ID NO: 14:

(i) SEQUENCE CHARACTERISTICS:
            (A) LENGTH: 25 Base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 14:

CTGTGTTATA TCCCTAAAGT GGTGA                                             25

(2) INFORMATION FOR SEQ ID NO: 15:

(i) SEQUENCE CHARACTERISTICS:
            (A) LENGTH: 16 Base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 15:

CCCGTATGGC AACAGG                                                       16

(2) INFORMATION FOR SEQ ID NO: 16:

(i) SEQUENCE CHARACTERISTICS:
            (A) LENGTH: 17 Base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 16:

TGTGCATGTC ATGAGTG                                                      17

(2) INFORMATION FOR SEQ ID NO: 17:

(i) SEQUENCE CHARACTERISTICS:
            (A) LENGTH: 22 Base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 17:

TATTGGATAC TTGAATCTGC TG                                                22

(2) INFORMATION FOR SEQ ID NO: 18:

(i) SEQUENCE CHARACTERISTICS:
            (A) LENGTH: 21 Base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 18:

TGCATCACCT CACATAGGTT A                                                21

(2) INFORMATION FOR SEQ ID NO: 19:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

GGAAGAATCA AATAGACAAT                                                  20

(2) INFORMATION FOR SEQ ID NO: 20:

(i) SEQUENCE CHARACTERISTICS:
        (A) LENGTH: 24 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

GCTGGCCATA TATATATTTA AACC                                             24

(2) INFORMATION FOR SEQ ID NO: 21:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

CAGGTTCTGT CATAGGACTA                                                  20

(2) INFORMATION FOR SEQ ID NO: 22:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

TTCTGGAAAC CTACTCCTGA                                                  20

(2) INFORMATION FOR SEQ ID NO: 23:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

CAGAAAATTC TCTCTGGCTA                                                  20

(2) INFORMATION FOR SEQ ID NO: 24:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

CTCATGTTCC TGGCAAGAAT                                                  20

(2) INFORMATION FOR SEQ ID NO: 25:

(i) SEQUENCE CHARACTERISTICS:
        (A) LENGTH: 16 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

GCTCCCGGCT GGTTTT                                                      16

(2) INFORMATION FOR SEQ ID NO: 26:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

GCAGGAAATC GCAGGAACTT                                                  20

(2) INFORMATION FOR SEQ ID NO: 27:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

CTCTTTCTCT GACTCTGACC                                                  20

(2) INFORMATION FOR SEQ ID NO: 28:

(i) SEQUENCE CHARACTERISTICS:
        (A) LENGTH: 21 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

GACTTTCTAA GTTCTTGCCA G                                              21

(2) INFORMATION FOR SEQ ID NO: 29:

(i) SEQUENCE CHARACTERISTICS:

(A) LENGTH: 26 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 29:

AGCGCAGCAC CTCCCGGCGC CAGTTT                                                        26

(2) INFORMATION FOR SEQ ID NO: 30:

(i) SEQUENCE CHARACTERISTICS:
        (A) LENGTH: 27 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 30:

GCTGCTGCTG CCTGGGGCTA GTCTCTT                                                       27

(2) INFORMATION FOR SEQ ID NO: 31:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

TCGCCTCCAA GAATGTAAGT                                                               20

(2) INFORMATION FOR SEQ ID NO: 32:

(i) SEQUENCE CHARACTERISTICS:
        (A) LENGTH: 21 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

TCTGCATTTT AACTATGGCT C                                                             21

(2) INFORMATION FOR SEQ ID NO: 33:

(i) SEQUENCE CHARACTERISTICS:
        (A) LENGTH: 21 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

TGACTACTTT TGACTTCAGC C                                                             21

(2) INFORMATION FOR SEQ ID NO: 34:

(i) SEQUENCE CHARACTERISTICS:
        (A) LENGTH: 22 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

AACCATTCAA CATTTTTAAC CC                                                        22

(2) INFORMATION FOR SEQ ID NO: 35:

(i) SEQUENCE CHARACTERISTICS:
            (A) LENGTH: 21 Base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 35:

ATTAACTTCC TACACCACAA C                                                         21

(2) INFORMATION FOR SEQ ID NO: 36:

(i) SEQUENCE CHARACTERISTICS:
            (A) LENGTH: 19 Base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 36:

GTAGAGCAAG ACCACCTTG                                                            19

(2) INFORMATION FOR SEQ ID NO: 37:

(i) SEQUENCE CHARACTERISTICS:
            (A) LENGTH: 29 Base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 37:

CGGTTATCCC AGTTCGGCCT CTCTGGGAT                                                 29

(2) INFORMATION FOR SEQ ID NO: 38:

(i) SEQUENCE CHARACTERISTICS:
            (A) LENGTH: 28 Base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 38:

TCCACCTCCC GCTCAGTCAG ACTGCGCT                                                  28

(2) INFORMATION FOR SEQ ID NO: 39:

(i) SEQUENCE CHARACTERISTICS:
            (A) LENGTH: 32 Base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 39:

```
GCAGCTATAA TGACTAGAAT GAAGTCCTAC TG                                    32

(2) INFORMATION FOR SEQ ID NO: 40:

(i) SEQUENCE CHARACTERISTICS:
        (A) LENGTH: 36 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 40:

TTGAATTAAA GACTTGTTTA AACACAAAAT TTAGAC                                36

(2) INFORMATION FOR SEQ ID NO: 41:

(i) SEQUENCE CHARACTERISTICS:
        (A) LENGTH: 19 Base pairs
        (B) TYPE: nucleic acid
        (C) STRANDEDNESS: single
        (D) TOPOLOGY: linear (ii) MOLECULE TYPE:DNA (xi) SEQUENCE DESCRIPTION: SEQ ID NO: 41:

TGGCGAGACT CCATCAAAG                                                   19

(2) INFORMATION FOR SEQ ID NO: 42:

(i) SEQUENCE CHARACTERISTICS:
        (A) LENGTH: 22 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 42:

CTTTTTAAGC TGCAACAATT TC                                               22

(2) INFORMATION FOR SEQ ID NO: 43:

(i) SEQUENCE CHARACTERISTICS:
        (A) LENGTH: 19 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 43:

CTCCTCCCTA CTTACTTGT                                                   19

(2) INFORMATION FOR SEQ ID NO: 44:

(i) SEQUENCE CHARACTERISTICS:
        (A) LENGTH: 19 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 44:

AATTAACAAG GTGTGGTGG                                                   19
```

```
(2) INFORMATION FOR SEQ ID NO: 45:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 45:

GCACTTTCCT CAACTCTACA                                          20

(2) INFORMATION FOR SEQ ID NO: 46:

(i) SEQUENCE CHARACTERISTICS:
        (A) LENGTH: 20 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 46:

AACAGCTCCT TTAATGGCAG                                          20

(2) INFORMATION FOR SEQ ID NO: 47:

(i) SEQUENCE CHARACTERISTICS:
        (A) LENGTH: 24 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 47:

AGGGATACTA TTCAGCCCGA GGTG                                     24

(2) INFORMATION FOR SEQ ID NO: 48:

(i) SEQUENCE CHARACTERISTICS:
        (A) LENGTH: 22 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 48:

ACTGCCACTC CTTGCCCCAT TC                                       22

(2) INFORMATION FOR SEQ ID NO: 49:

(i) SEQUENCE CHARACTERISTICS:
        (A) LENGTH: 21 Base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 49:

CCCACAGCCT ATTCAGAACA C                                        21

(2) INFORMATION FOR SEQ ID NO: 50:

(i) SEQUENCE CHARACTERISTICS:
        (A) LENGTH: 20 Base pairs
```

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 50:

GTTGACTGCT GAACGGCTGC                                                    20
```